United States Patent
Waimberk et al.

(10) Patent No.: US 10,070,935 B2
(45) Date of Patent: Sep. 11, 2018

(54) SHARPS CONTAINER WITH SLIDING DOOR SHARPS DISPOSAL LID

(71) Applicant: Medline Industries, Inc., Mundelein, IL (US)

(72) Inventors: Monica Waimberk, Chicago, IL (US); James Burgess, Mundelein, IL (US); Scott Bedoe, McHenry, IL (US)

(73) Assignee: Medline Industries, Inc., Northfield, IL (US)

( * ) Notice: Subject to any disclaimer, the term of this patent is extended or adjusted under 35 U.S.C. 154(b) by 874 days.

(21) Appl. No.: 14/341,199

(22) Filed: Jul. 25, 2014

(65) Prior Publication Data
US 2016/0022362 A1    Jan. 28, 2016

(51) Int. Cl.
*B65D 43/20*    (2006.01)
*A61B 50/36*    (2016.01)
*B65D 43/22*    (2006.01)
*A61B 50/00*    (2016.01)

(52) U.S. Cl.
CPC ...... *A61B 50/362* (2016.02); *A61B 2050/006* (2016.02); *A61B 2050/008* (2016.02); *A61B 2050/0059* (2016.02); *A61B 2050/0076* (2016.02)

(58) Field of Classification Search
CPC ........ B65D 43/20; B65D 43/22; B65D 43/24; A61B 51/362; A61B 2050/0059; A61B 2050/006; A61B 2050/0076; A61B 2050/008
USPC .......... 220/345.5, 345.1, 345.2, 254.9, 345.3
See application file for complete search history.

(56) References Cited

U.S. PATENT DOCUMENTS

| | | | | |
|---|---|---|---|---|
| 2,223,023 A | * | 11/1940 | Weilemann | E06B 3/4672 220/345.5 |
| D282,286 S | | 1/1986 | Gianni | |
| D292,037 S | | 9/1987 | Hanifl | |
| 4,757,913 A | * | 7/1988 | Yerman | B65D 43/20 220/345.5 |
| 4,762,242 A | * | 8/1988 | Harris | E04H 5/06 137/234.6 |

(Continued)

OTHER PUBLICATIONS

Muller, David "Restriction Requirement", U.S. Appl. No. 29/497,598, filed Jul. 25, 2014; dated Sep. 14, 2016.

(Continued)

*Primary Examiner* — J. Gregory Pickett
*Assistant Examiner* — Niki M Eloshway
(74) *Attorney, Agent, or Firm* — Philip H. Burrus, IV

(57) ABSTRACT

A lid (100) for a container (1901) includes a first sliding door (102) and a second sliding door (103). A lid body (101) has a container engaging section (104) and an interior section (103) having a sliding surface (120) and a sharps disposal aperture (119). The second sliding door interlocks between the sliding surface and the first sliding door. The first sliding door and the second sliding door are selectively slidable between: an open position (1100) with a minor protuberance (124) and the major protuberance (125) disposed beneath the second sliding door; a partially closed position (1500) with an edge (701) of the second sliding door disposed between the minor protuberance and the major protuberance; and a closed position (1700) with the major protuberance disposed between the edge of the second sliding door and the minor protuberance.

20 Claims, 15 Drawing Sheets

(56) References Cited

U.S. PATENT DOCUMENTS

| | | | |
|---|---|---|---|
| 4,842,138 A | 6/1989 | Snadel et al. | |
| D302,291 S | 7/1989 | Heubel et al. | |
| 5,024,326 A | 6/1991 | Sandel et al. | |
| 5,035,703 A | 7/1991 | Baskas | |
| 5,107,990 A | 4/1992 | Wicherski et al. | |
| D330,765 S | 11/1992 | Laws | |
| 5,165,564 A | 11/1992 | Prout et al. | |
| 5,415,315 A | 5/1995 | Ramirez | |
| D436,171 S | 1/2001 | Gaba et al. | |
| D447,233 S | 8/2001 | Bickel et al. | |
| 6,435,587 B1* | 8/2002 | Flowerday | B60N 3/08 220/345.5 |
| D474,840 S | 5/2003 | Crawford | |
| D482,448 S | 11/2003 | Crawford | |
| D485,906 S | 1/2004 | Danssaert et al. | |
| D502,993 S | 3/2005 | McArthur et al. | |
| D518,173 S | 3/2006 | Coates | |
| 7,584,843 B2* | 9/2009 | Kutsch | B65D 1/22 206/267 |
| 8,087,533 B2* | 1/2012 | Sellers | E06B 3/4663 220/345.1 |
| D694,882 S | 12/2013 | Stark | |
| D699,843 S | 2/2014 | Stark | |
| 8,851,282 B2* | 10/2014 | Brunner | B25H 3/028 206/372 |
| 2006/0037484 A1 | 2/2006 | Dixon et al. | |
| 2011/0259152 A1 | 10/2011 | Kovacs | |

OTHER PUBLICATIONS

Muller, David "Restriction Requirement", U.S. Appl. No. 29/497,599, filed Jul. 25, 2014; dated Sep. 14, 2016.

Muller, David "Notice of Allowance", U.S. Appl. No. 29/497,599, filed Jul. 25, 2014; dated Dec. 9, 2016.

"Medline Catalog", 8 Gallon Sharpstar by MarketLab; Medline Catalog; http://www.medline.com/catalog/catalog.jsp; Unknown Publication date but believed to be prior to present application filing date.

"Medline Catalog", Biomax Large Containers w/Sealing Gasket by Covidien; Medline Catalog; http://www.medline.com/catalog/catalog.jsp; Unknown Publication date but believed to be prior to present application filing date.

"Medline Catalog", Chemotherapy Sharps Collectors by Becton Dickinson; Medline Catalog; http://www.medline.com/catalog/catalog.jsp; Unknown Publication date but believed to be prior to present application filing date.

"Medline Catalog", Hinged Top Waste Sharps Containers by Covidien; Medline Catalog; http://www.medline.com/catalog/catalog.jsp; Unknown Publication date but believed to be prior to present application filing date.

"Medline Catalog", Large Hands-Free Sharps Cart by Marketlab; Medline Catalog; http://www.medline.com/catalog/catalog.jsp; Unknown Publication date but believed to be prior to present application filing date.

"Medline Catalog", Large Pg-II Containers; Medline Catalog; http://www.medline.com/catalog/catalog.jsp; Unknown Publication date but believed to be prior to present application filing date.

"Medline Catalog", Large Volume Sharps Containers by Bemes Inc; Medline Catalog; http://www.medline.com/catalog/catalog.jsp; Unknown Publication date but believed to be prior to present application filing date.

"Medline Catalog", Large Volume Sharps Containers by Bemis Mfg; Medline Catalog; http://www.medline.com/catalog/catalog.jsp; Unknown Publication date but believed to be prior to present application filing date.

"Medline Catalog", Mobile Sharps Containment by Marketlab; Medline Catalog; http://www.medline.com/catalog/catalog.jsp; Unknown Publication date but believed to be prior to present application filing date.

"Medline Catalog", Multipurpose Sharps Containers; Medline Catalog; http://www.medline.com/catalog/catalog.jsp; Unknown Publication date but believed to be prior to present application filing date.

"Medline Catalog", PG2 Slide Lid Sharps Containers by Medtronic; Medline Catalog; http://www.medline.com/catalog/catalog.jsp; Unknown Publication date but believed to be prior to present application filing date.

"Medline Catalog", Renewables Sharps Disposal Containers by Medtronic; Medline Catalog; http://www.medline.com/catalog/catalog.jsp; Unknown Publication date but believed to be prior to present application filing date.

"Medline Catalog", Sharps Container/Accessories by Becton Dickinson; Medline Catalog; http://www.medline.com/catalog/catalog.jsp; Unknown Publication date but believed to be prior to present application filing date.

"Medline Catalog", Sharps Containers by Medegen Medical; Medline Catalog; http://www.medline.com/catalog/catalog.jsp; Unknown Publication date but believed to be prior to present application filing date.

"Medline Catalog", Sharps In-Room Mailbox Style Lid Containers by Medtronic; Medline Catalog; http://www.medline.com/catalog/catalog.jsp; Unknown Publication date but believed to be prior to present application filing date.

"Medline Catalog", SharpSafety Biohazard Waste Containers by Medtronic; Medline Catalog; http://www.medline.com/catalog/catalog.jsp; Unknown Publication date but believed to be prior to present application filing date.

"Medline Catalog", SharpSafety Gasketed Hinged Lid Containers by Medtronic; Medline Catalog; http://www.medline.com/catalog/catalog.jsp; Unknown Publication date but believed to be prior to present application filing date.

"Medline Catalog", SharpSafety Hinged Lid Sharps Containers by Medtronic; Medline Catalog; http://www.medline.com/catalog/catalog.jsp; Unknown Publication date but believed to be prior to present application filing date.

"Medline Catalog", SharpSafety RCRA Hazardous Waiste (sic) Containers by Medtronic; Medline Catalog; http://www.medline.com/catalog/catalog.jsp; Unknown Publication date but believed to be prior to present application filing date.

"Medline Catalog", SharpSafety Transpotable Sharps Containers by Covidien; Medline Catalog; http://www.medline.com/catalog/catalog.jsp; Unknown Publication date but believed to be prior to present application filing date.

"Medline Catalog", Slide Lid SharpSafety Sharps Containers by Medtronic; Medline Catalog; http://www.medline.com/catalog/catalog.jsp;.Unknown Publication date but believed to be prior to present application filing date.

"Medline Catalog", Slide Lid Sharps-A-Gator Containers by Medtronic; Medline Catalog; http://www.medline.com/catalog/catalog.jsp; Unknown Publication date but believed to be prior to present application filing date.

Muller, David , "NonFinal OA", U.S. Appl. No. 29/497,598; Filed Jul. 25, 2014; dated Feb. 14, 2017.

Muller, David , "Notice of Allowance", U.S. Appl. No. 29/497,599; Filed Jul. 25, 2014; dated Mar. 17, 2017.

* cited by examiner

SHARPS CONTAINER WITH SLIDING DOOR SHARPS DISPOSAL LID

BACKGROUND

Technical Field

This disclosure relates generally to containers, and more particularly to containers with lids.

Background Art

Medical practices, hospitals, doctors, and other health care practitioners must follow specific procedures when disposing of medical waste. Such waste is generally classified into different categories. Different containers can be provided for collecting the different classifications of medical waste. For example, soft waste such as gauze, bandages, or towels may be placed in red-colored containers. By contrast, rigid waste, such as medical devices and hardware, may be collected in different containers.

Items with sharp points or edges, including scissors, needles, scalpels, blades, shavers, catheter needles, trocars, and other puncturing or cutting items are referred to as "sharps" due to their cutting or puncturing components. Such devices are collected in rigid containers known as "sharps containers." Sharps must be immediately disposed within a sharps container after use to prevent the cutting or puncturing components from cutting or puncturing someone, potentially cross contaminating the person with a disease from a patient. In addition to cutting and puncturing tools, sharps containers can be used to collect other items, including vials, glass, and pharmaceutical waste products. Sharps containers are available in various sizes ranging from small tabletop containers to larger floor-standing containers. Some sharps containers are difficult to use. It would be advantageous to have an improved sharps container.

Figure 1:
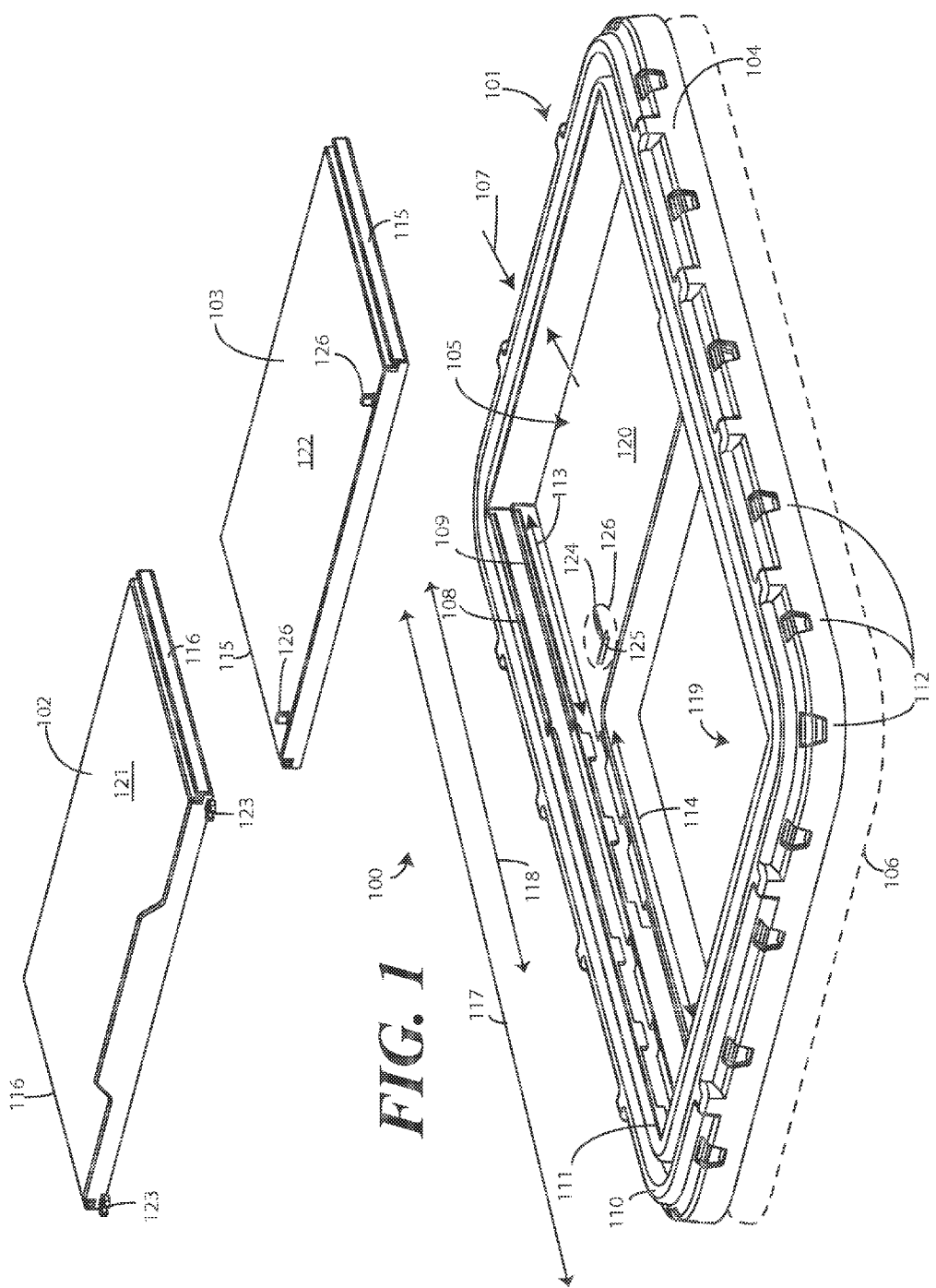
FIG. 1 illustrates an exploded view of one explanatory lid for a sharps container in accordance with one or more embodiments of the disclosure.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present disclosure.

DETAILED DESCRIPTION OF THE DRAWINGS

Embodiments of the disclosure are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Also, reference designators shown herein in parenthesis indicate components shown in a figure other than the one in discussion. For example, talking about a device (10) while discussing figure A would refer to an element, 10, shown in figure other than figure A. It is expected that one of ordinary skill, notwithstanding possibly significant effort and many design choices motivated by, for example, available time, current technology, and economic considerations, when guided by the concepts and principles disclosed herein will be readily capable of generating sharps containers and lids described below with minimal experimentation.

In this document, relational terms such as first and second, top and bottom, and the like may be used solely to distinguish one entity or action from another entity or action without necessarily requiring or implying any actual such relationship or order between such entities or actions. This is especially true due to the fact that there is a first sliding door and a second sliding door, and sometimes in the description below one sliding door, e.g., the top sliding door will be referred to as the "first sliding door" or the "second sliding door" due to the fact that relational terms solely distinguish one entity from another without requiring a particular relationship or order.

Embodiments of the disclosure contemplate that sharps containers can be classified in different ways. Some are intended to receive sharps for reuse after appropriate sterilization. The lid of a sharps container designated for sharps reuse is generally designed so as to be easily removable. Other sharps containers are classified for disposal. The latter type of sharps container is generally designed with a lid that is not to be reopened once closed.

Embodiments of the disclosure contemplate that there can be problems associated with the use of sharps containers classified for disposal. If, for example, a health care services provider accidentally closes the lid inadvertently, it cannot be reopened. If the lid were accidentally closed after receiving, say, only one or two sharps placed into the container, the health care services provider would need to fetch another sharps container to continue depositing sharps therein. After an ordinary surgical procedure, there can be many sharps requiring disposal. Having to retrieve additional sharps containers due to inadvertent closure is burdensome. Moreover, if a health care services provider has to leave a sterile environment to retrieve a new container, the sterile field may be compromised.

Embodiments of the disclosure provide a solution to this problem. In one embodiment, a lid for a sharps container includes a first sliding door and a second sliding door. The first sliding door and second sliding door engage a first track and a second track of a container engaging section of a lid body so as to be slidable therein. An interior section of the lid body, which extends from the container engaging section within a perimeter of the lid defined by the container engaging section, includes a sharps disposal aperture and a sliding surface. The sliding surface includes one or more protuberances. In one embodiment, the sliding surface includes a minor protuberance disposed along the interior section and a major protuberance disposed along the interior section proximally with the minor protuberance.

In one embodiment, the second sliding door interlocks between the sliding surface and the first sliding door. In this configuration, the first sliding door and the second sliding door are selectively slidable between one of three positions: an open position, a partially closed position, and a closed position. When in the open position, in one embodiment, the minor protuberance and the major protuberance are disposed beneath at least the second sliding door, and in one embodiment are disposed beneath both the first sliding door and the second sliding door. When in the partially closed position, an edge of the second sliding door is disposed between the minor protuberance and the major protuberance. When in the closed position, the major protuberance is disposed between the edge of the second sliding door and the minor protuberance.

Advantageously, the ability to position the sliding doors in the partially closed position with the edge of the second sliding door disposed between the minor protuberance and the major protuberance allows a user to almost completely close the sharps container without the sliding doors locking shut. As the major protuberance is larger than the minor protuberance, it serves as a partial mechanical stop to prevent the sliding doors from transitioning from the partially closed position to the closed position as the force required to slide the sliding doors past the major protuberance is greater than that required to slide the sliding doors past the minor protuberance. Consequently, a user can easily transition the sliding doors between the partially closed position and the open position without inadvertently locking the sliding doors in the closed position. When finished with the sharps container, the user simply slides the sliding doors across the sharps receiving aperture. In the closed position, the major protuberance, and optionally one or more cantilevered hooks, perdurably lock the first sliding door and the second sliding door in place to ensure that any sharps disposed within the container remain therein.

Turning now to FIG. 1, illustrated therein is an exploded view of a lid 100 for a sharps container. When the lid 100 is coupled to a sharps container, as will be described below with reference to FIG. 17, the assembly can be used to reliably dispose of sharps devices by securing those devices within the sharps container for incineration or other disposal methods.

The illustrative lid 100 of FIG. 1 includes a lid body 101, a first sliding door 102, and a second sliding door 103. Each of the lid body 101, the first sliding door 102, and the second sliding door 103 can be manufactured from a thermoplastic material by way of an injection molding process, a vacuum molding process, or other tooling process. For example, in one embodiment, each of the lid body 101, the first sliding door 102, and the second sliding door 103 is manufactured from polypropylene. In another embodiment, each of the lid body 101, the first sliding door 102, and the second sliding door 103 is manufactured from polyethylene. In another embodiment, each of the lid body 101, the first sliding door 102, and the second sliding door 103 can alternatively be thermally formed on a mold from a softer thermoplastic, such as styrene or polystyrene. In another embodiment, the lid body 101, the first sliding door 102, and the second sliding door 103 can be formed by pouring a quick setting plastic, epoxy, or resin on a mold. It will be obvious to those of ordinary skill in the art having the benefit of this disclosure that other suitable semi-rigid materials may be substituted for the thermoplastic. Further, the lid body 101, the first sliding door 102, and the second sliding door 103 may each be made from different materials, or combinations of different materials as well.

The lid body 101 comprises a container engaging section 104 and an interior section 105. In one embodiment, the container engaging section 104 defines a perimeter 106 of the lid 100 by defining a perimeter 106 of the lid body 101. While the container engaging section 104 defines a perimeter 106 of the container lid, i.e., a continuous segment forming the outer boundary of the lid 100 and lid body 101, it should be noted that the container engaging section 104 has associated therewith a width 107 sufficient to incorporate one or more features. Examples of the features include a first track 108, a second track 109, a recess 110 to receive an edge of a sharps container, and a sharps deposition well wall 111. The container engaging section 104 includes a container receiving well, configured as concave receiver, and disposed beneath the recess 110 in one or more embodiments.

In this illustrative embodiment, the container engaging section 104 is a contoured, substantially rectangular (neglecting the slight curvature at the corners) member that surrounds, and that is oriented substantially orthogonally with, the interior section 105. In one embodiment, the container engaging section 104 comprises a substantially rectangular (when viewed in plan view) sidewall member surrounding the interior section 105. In operation, the container engaging section 104 functions as a "canister connector" in that it is configured to attach to a sharps collection container. In one embodiment, container engaging section 104 can have one or more compliant coupling members 112 disposed therealong. In the illustrative embodiment of FIG. 1, the compliant coupling members 112 are configured as cantilever members extending from the exterior of the container engaging section 104 to "clamp" the edge of a sharps container so as to retain the lid 100 to the sharps container. Accordingly, the lid 100 is configured to connect to, and essentially seal the opening of, a sharps container. In one or more embodiments, the compliant coupling members 112 are "one way" coupling members in that when the lid 100 is coupled to the sharps container it is not removable without tearing or otherwise damaging the lid 100.

In one embodiment, the first track 108 is to receive the first sliding door 102. Similarly, the second track 109 is to receive the second sliding door 103. In this illustrative embodiment, the first track 108 is longer than the second track 109. The first track 108 of this embodiment extends substantially along all of the width 117 of the lid 100, while the second track 109 extends along only a portion 118 of the width 117. As will be shown in more detail below, this difference in lengths of the first track 108 and the second track 109 facilitates interlocking of the first sliding door 102 and the second sliding door 103 to allow the two to work in tandem to cover a sharps disposal aperture 119 of the interior section 105 when the first sliding door 102 and the second sliding door 103 are moved to the closed position.

Figure 2:
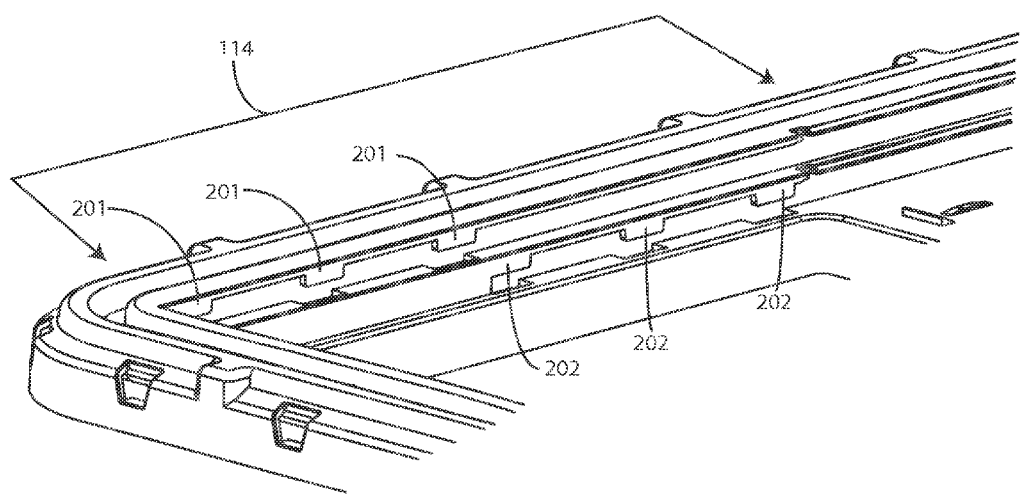
FIG. 2 illustrates a portion of a container engaging section of one explanatory lid in accordance with one or more embodiments of the disclosure.

In one embodiment, edges 115,116 of the first sliding door 102 and the second sliding door 103 can be inserted in receiving sections 113 of the first track 108 and the second track 109, respectively. The first sliding door 102 and the second sliding door 103 can then be slid to engaging sections 114 of the first track 108 and the second track 109. Turning briefly to FIG. 2, illustrated therein is a magnified view of the engaging sections 114 of the first track 1089 and the second track 109.

As shown in FIG. 2, in one embodiment each of the first track 108 and the second track 109 includes one or more flanges 201,202 along the engaging section 114 to retain the first sliding door (102) and the second sliding door (103) within the first track 108 and the second track 109, respectively. In this illustrative embodiment, the one or more flanges 201,202 are discontinuous flanges, in that three flanges are disposed along the first track 108 and the second track 109, respectively. In other embodiments, the one or more flanges 201,202 can comprise a single, continuous flange rather than the discontinuous flanges shown in FIG. 2.

Figure 3:
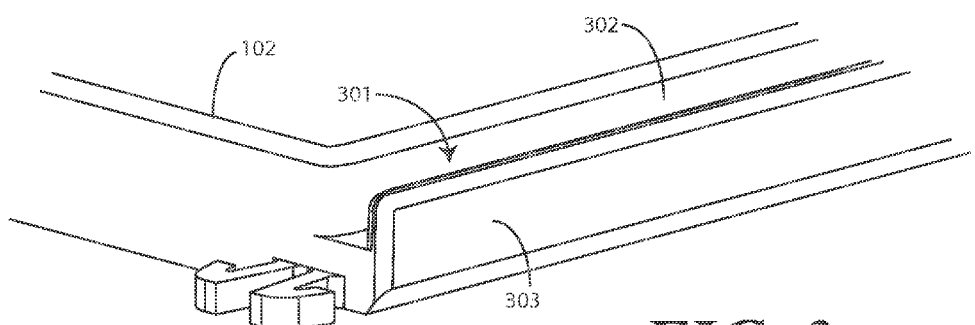
FIG. 3 illustrates a portion of one explanatory sliding door in accordance with one or more embodiments of the disclosure.

Turning briefly now to FIG. 3, in one embodiment each of the first sliding door 102 or the second sliding door (103) includes a groove 301 to receive the one or more flanges (201,202) if the engaging section (114) of the first track (108) and the second track (109) when the first sliding door 102 and the second sliding door (103) are coupled to the lid body (101). In this embodiment, the groove 301 is formed between an edge 302 of the sliding door and a vertically extending sidewall 303. Other mechanisms for coupling the first sliding door 102 or the second sliding door (103) to the lid body (101) will be obvious to those of ordinary skill in the art having the benefit of this disclosure.

Turning now back to FIG. 1, the interior section 105 of the lid, in one embodiment, extends from the container engaging section 104 interior of the perimeter 106 of the lid 100 defined by the container engaging section 104. In this illustrative embodiment, the interior section 105 defines a sliding surface 120 and the sharps disposal aperture 119. In one embodiment the sliding surface 120 is substantially planar so as to allow the second sliding door 103 to slide along the top of the sliding surface 120. The use of the term "substantially" in this document refers to something inclusive of manufacturing tolerances. Accordingly, a "substantially planar" surface may not be ideally planar, but may be planar inclusive of non-planar segments resulting to manufacturing or tooling tolerances.

In this illustrative embodiment, the sliding surface 120 has a smaller area—when viewed in plan view—than does the sharps disposal aperture 119. Said differently, in this illustrative embodiment the sliding surface 120 spans a minority, i.e., less than fifty percent of the area, of the interior section 105. By contrast, the sharps disposal aperture 119, into which sharps are passed when the lid 100 is coupled to a sharps container, spans a majority, i.e., more than fifty percent of the area, of the interior section 105. In one embodiment, the minority of the interior section 105 is equal to or less than one third of an area defined by the interior section 105 when viewed in plan view, i.e., the area within the perimeter 106. In one embodiment, the minority of the interior section 105 is between twenty percent and thirty-six percent of the area defined by the interior section 105.

Experimental testing has shown that by providing a sharps disposal aperture 119 spanning a majority, but less than two-thirds, of the interior section 105 provides ample room through which to pass sharps of various sizes. At the same time, the sharps disposal aperture is small enough that a user is less likely to come into contact with sharps disposed within the container. Embodiments of the disclosure contemplate that a primary function of any sharps container is to provide a receptacle for sharps that safely functions to prevent incidental contact between a user and a used sharp. When needles and/or surgical instruments are placed into a sharps container by passing them through the sharps disposal aperture 119, it is frequently the case that the sharps have been used to provide medical treatment to a patient and are thus exposed to blood, bodily fluids, or other substances that can communicate disease pathogens. Advantageously, the sizing of the sharps disposal aperture 119 and/or its ratio to the area of the sliding surface 120 work to prevent health care services providers or other users from accidentally coming into contact with the sharps, thereby potentially exposing them to infection.

To provide a dimensional context to one illustrative lid 100, in one embodiment, the sharps disposal aperture 119 measures about 215 millimeters by about 223 millimeters. By contrast, the sliding surface 120 measures about 215 millimeters by about 125 millimeters. These dimensions are illustrative only, as others will be readily apparent to those of ordinary skill in the art having the benefit of this disclosure.

On the subject of area, the first sliding door 102 defines a first sliding door major face 121. Similarly, the second sliding door 103 defines a second sliding door major face 122. In the illustrative embodiment of FIG. 1, each of the first sliding door major face 121 and the second sliding door major face 122 has an area that is less than the area of the sharps disposal aperture 119. Accordingly, neither the first sliding door 102 nor the second sliding door 103 could—alone—successfully cover the sharps disposal aperture 119. However, in one embodiment when interlocked, the first sliding door 102 and the second sliding door 103 together have a combined area that is greater than the area of the sharps disposal aperture 119.

Figure 4:
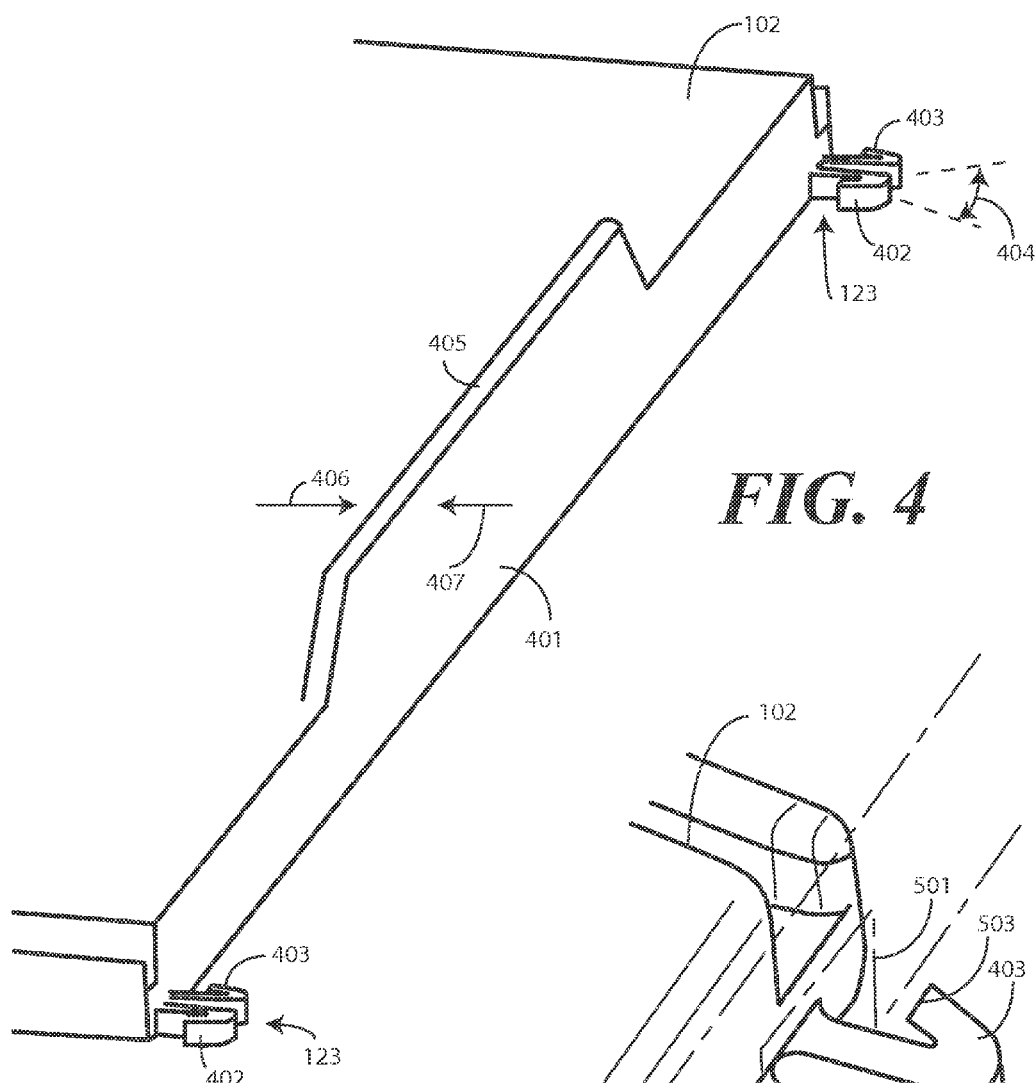
FIG. 4 illustrates another portion of one explanatory sliding door in accordance with one or more embodiments of the disclosure.
Figure 5:
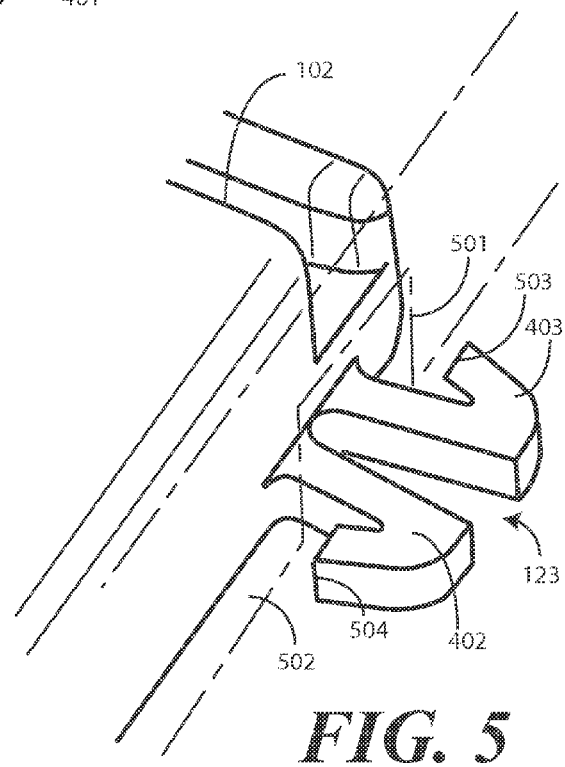
FIG. 5 illustrates explanatory cantilevered hooks for perdurably locking a sliding door to a container engaging portion of a lid in accordance with one or more embodiments of the disclosure.

In one embodiment, the first sliding door 102 includes one or more locking features 123. Turning now briefly to FIGS. 4-5, illustrated therein are magnified views of the one or more locking features 123.

As shown in FIG. 4, in one embodiment the first sliding door 102 includes two locking features 123. However, in other embodiments the first sliding door 102 includes only one locking feature 123. In still other embodiments, the first sliding door 102 can include three or more locking features 123. The locking features 123 can be the same or different. Accordingly, different types of locking features can be used to lock the first sliding door 102 in the closed position.

In the illustrative embodiment of FIG. 4, each locking feature 123 comprises a pair of cantilevered hooks 402,403 extending from a front side edge 401 of the first sliding door 102. In this illustrative embodiment, each cantilevered hook 402,403 extends from the front side edge 401 of the first sliding door 102 at a non-orthogonal angle such that there is a separation angle 404 between the cantilevered hooks 402,403. As with the compliant coupling members (112) discussed above, in on embodiment the locking feature 123 is configured to be a "one way" locking mechanism so that the lid (100) can be used with sharps containers classified for disposal by providing a lid (100) that is not to be reopened once closed. The separation angle 404 works to provide the one way locking function.

As shown in FIG. 5, when the first sliding door 102 is selectively moved to the closed position, each cantilevered hook 402,403 of the locking mechanism deflects through an aperture 501 in an interior sidewall 502 of the container engaging section (104). The cantilevered hooks 402,403 then un-deflect such that rear portions 503,504 of the cantilevered hooks 402,403 then are retained against the interior sidewall 502 to perdurably lock the first sliding door 102 to the interior sidewall 502 of the container engaging section (104). As will be shown in more detail below, in one embodiment this occurs when the first sliding door 102 and the second sliding door (103) are in the closed position.

Turning back to FIG. 4, in one embodiment the first sliding door 102 includes a flange 405. In one embodiment the flange 405 serves as a handle or finger grip by which the first sliding door 102 can be selectively slid. For example, in one embodiment the first sliding door 102 is to slide toward the partially closed or closed position when a closing force 406 is applied to the flange 405. By contrast, in one embodiment the first sliding door 102 is to slide toward the open position when an opening force 407 is applied to the flange 405. In one embodiment, once the first sliding door 102 reaches the closed position, with the locking feature 123 successfully engaged with the interior sidewall (502) of the container engaging section (104), it cannot be returned to the open or partially closed position without destroying one or more lid components. This allows for sharps containers classified for disposal by providing a lid (100) that is not to be reopened once closed.

Turning now back to FIG. 1, in one embodiment a minor protuberance 124 and a major protuberance 125 are disposed along the interior section 105. In this illustrative embodiment, the minor protuberance 124 and the major protuberance 125 are disposed along the sliding surface 120. However, they can be disposed in other locations as well as will be described below with reference to FIG. 9. The major protuberance 125 is major, while the minor protuberance is minor 124, because the major protuberance 125 extends distally farther from the sliding surface 120 than does the minor protuberance 124.

In this illustrative embodiment, the major protuberance 125 and the minor protuberance 124 are proximally located with each other. As used herein, proximally located means located within less than an inch of each other, and preferably less than a half-inch of each other. The distance between the major protuberance 125 and the minor protuberance 124 defines the distance between the partially closed position and the closed position of the first sliding door 102 and the second sliding door 103. For maximum protection of the user when the first sliding door 102 and the second sliding door 103 are in the partially closed position, the major protuberance 125 and the minor protuberance 124 should be proximally located within an area of about a half-inch or less.

Figure 6:
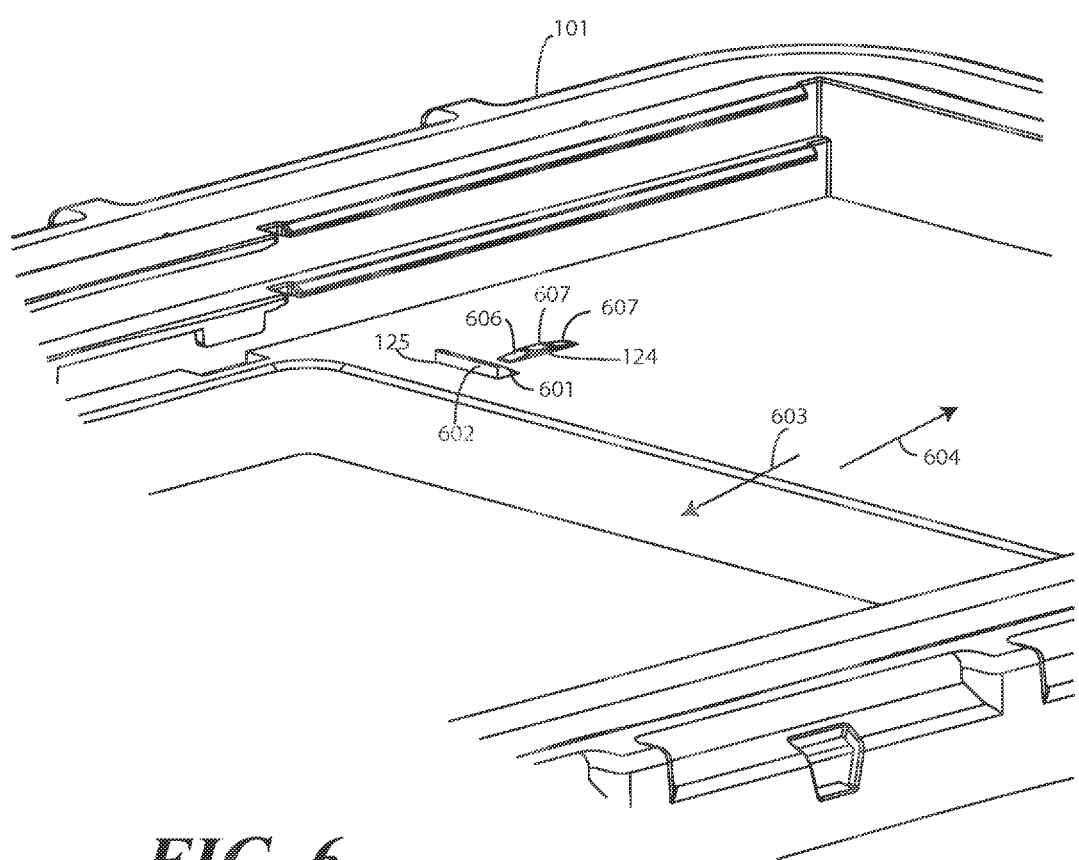
FIG. 6 illustrates an explanatory portion of an interior section extending from a container engaging section within a perimeter of a lid that includes a sharps disposal aperture, a sliding surface, a minor protuberance, and a major protuberance in accordance with one or more embodiments of the disclosure.

Turning briefly to FIG. 6, illustrated therein is a magnified portion of the lid body 101 illustrating one embodiment of the minor protuberance 124 and the major protuberance 125 in accordance with one or more embodiments of the disclosure. In this illustrative embodiment, the major protuberance 125 defines a single-sided ramp having a leading inclined surface 601 and a trailing vertical surface 602. This causes the major protuberance 125 to be a one-way protuberance that allows an edge of the second sliding door (103) to pass in the closing direction 603 by passing over the leading inclined surface 601. However, the trailing vertical surface 602 precludes the edge of the second sliding door (103) from translating in the opening direction 604 once in the closed position.

In this illustrative embodiment, the minor protuberance 124 comprises a double-sided ramp, having inclined surfaces 605,606 on both the leading and trailing edges. There is optionally a flat apogee 607 disposed between the leading and trailing edges. Providing inclined surfaces 605,606 on both the leading side and the trailing side allows an edge of the second sliding door (103) to relatively easily pass over the minor protuberance 124 between the open position and the partially closed position without moving haphazardly so as to be inadvertently opened or closed.

Figure 9:
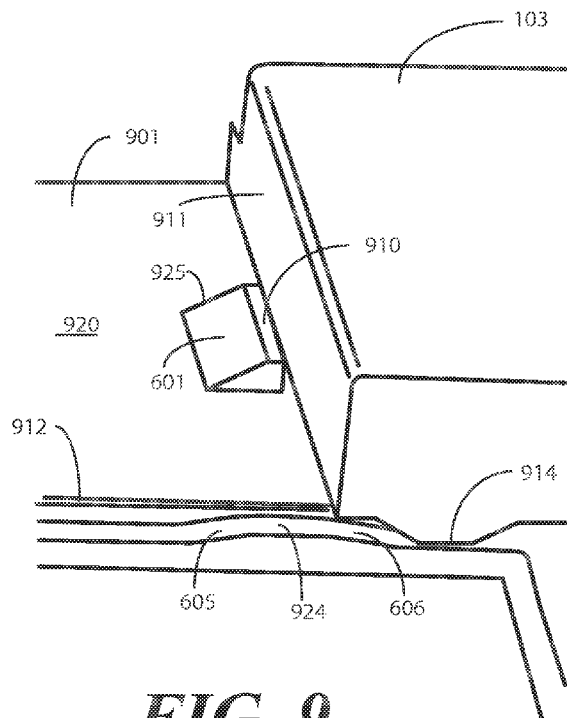
FIG. 9 illustrates an alternate interior section of a lid that includes a sliding surface, a minor protuberance, and a major protuberance in accordance with one or more embodiments of the disclosure.

To illustrate how embodiments of the disclosure can vary, turning now briefly to FIG. 9, illustrated therein is a magnified portion of another sliding surface 920 of another container body 901 illustrating another embodiment of the minor protuberance 924 and the major protuberance 925 in accordance with one or more embodiments of the disclosure. In this illustrative embodiment, as with the embodiment of FIG. 6, the major protuberance 925 defines a single-sided ramp having a leading inclined surface 601 and a trailing vertical surface, which is biased against a rear sidewall 911 of the second sliding door 103. This particular major protuberance 925 also includes a flat apogee 910 disposed between the trailing vertical surface and the leading inclined surface 601. The trailing vertical surface becomes biased against the rear sidewall 911 of the second sliding door 103 when the second sliding door 103 is in the closed position to retain the second sliding door 103 in the closed position.

In this illustrative embodiment, as with the embodiment of FIG. 6, the minor protuberance 924 comprises a double-sided ramp, having inclined surfaces 605,606 on both the leading and trailing edges. However, in contrast to the embodiment of FIG. 6, the minor protuberance 924 is recessed beneath the sliding surface 920. In this embodiment, the minor protuberance 924 is disposed within a groove 912 passing along the sliding surface 920. The second sliding door 103 then defines a flange 914 to insert into the groove 912 to engage the minor protuberance 924 when the second sliding door 103 transitions from the open position to the partially closed position. The engagement of the flange 914 and minor protuberance 924 is similar to that described above with reference to FIG. 6.

Turning now back to FIG. 1, in one embodiment the second sliding door 103 comprises one or more interlocking protrusions 126 to retain the second sliding door 103 interlocked between the sliding surface 120 and the first sliding door 102 when the first sliding door 102 slides relative to the second sliding door 103. This interlocking relationship is shown in FIG. 10.

Figure 10:
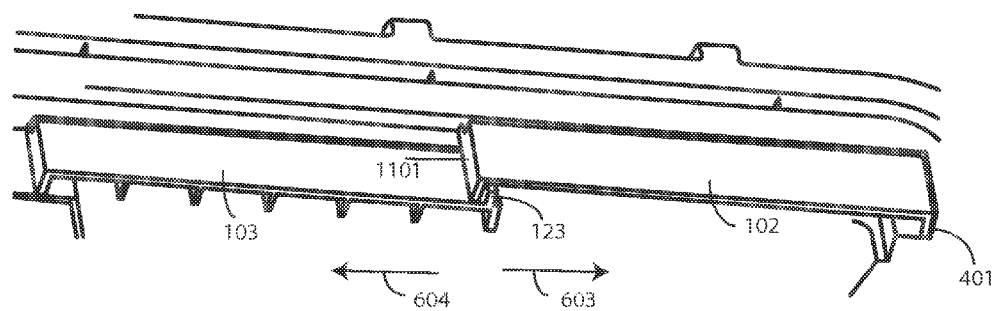
FIG. 10 illustrates a first sliding door interlocked between a second sliding door and a sliding surface of an interior section of a lid in accordance with one or more embodiments of the disclosure.

Turning briefly to FIG. 10, the first sliding door 102 and the second sliding door 103 are shown in the closed position. The interlocking protrusions 126 to retain the second sliding door 103 interlocked between the sliding surface 120 and the first sliding door 102 as shown. When the first sliding door 102 moves in the closing direction 603, the rear sidewall 1011 of the first sliding door 102 engages the interlocking protrusions 126 to pull the second sliding door 103 to the partially closed position or the closed position. Conversely, when the first sliding door 102 moves in the opening direction 604, the front side edge 401 of the first sliding door 102 engages the interlocking protrusions 126 to pull the second sliding door 103 toward the open position.

Turning now back to FIG. 1, in one embodiment the second sliding door 103 is to interlock between the sliding surface 120 and the first sliding door 102 with edges 115,116 of the first sliding door 102 and the second sliding door 103 inserted in receiving sections 113 of the first track 108 and the second track 109, respectively, and with the first sliding door 102 and the second sliding door 103 slid to the engaging sections 114 of the first track 108 and the second track 109. This will be shown in more detail below with reference to FIGS. 12-18. From this configuration, the first sliding door 102 and the second sliding door 103 are selectively slidable between an open position, a partially closed position, and a closed position.

In one embodiment, when in the open position the minor protuberance 124 and the major protuberance 125 disposed beneath at least the second sliding door 103, and in one embodiment are disposed beneath both the first sliding door 102 and the second sliding door 103. In one embodiment, when in the partially closed position, an edge of the second sliding door 103 is disposed between the minor protuberance 124 and the major protuberance 125. In one embodiment, when in the closed position the major protuberance 125 is disposed between the edge of the second sliding door 103 and the minor protuberance 124.

Advantageously, this provides the ability to position the sliding doors in the partially closed position with the edge of the second sliding door 103 disposed between the minor protuberance 124 and the major protuberance 125, thereby allowing a user to almost completely close the sharps container without the sliding doors locking shut. Consequently, a user can easily transition the sliding doors between the partially closed position and the open position without inadvertently locking the sliding doors in the closed position. When finished with the sharps container, the user simply slides the sliding doors across the sharps disposal aperture 119 with an edge of the second sliding door 103 passing over the major protuberance 125 and the locking feature 123 engaging the interior sidewall (502) of the container engaging section 104, thereby perdurably locking the first sliding door 102 and the second sliding door 103 in place to ensure that any sharps disposed within the container remain therein.

Figure 7:
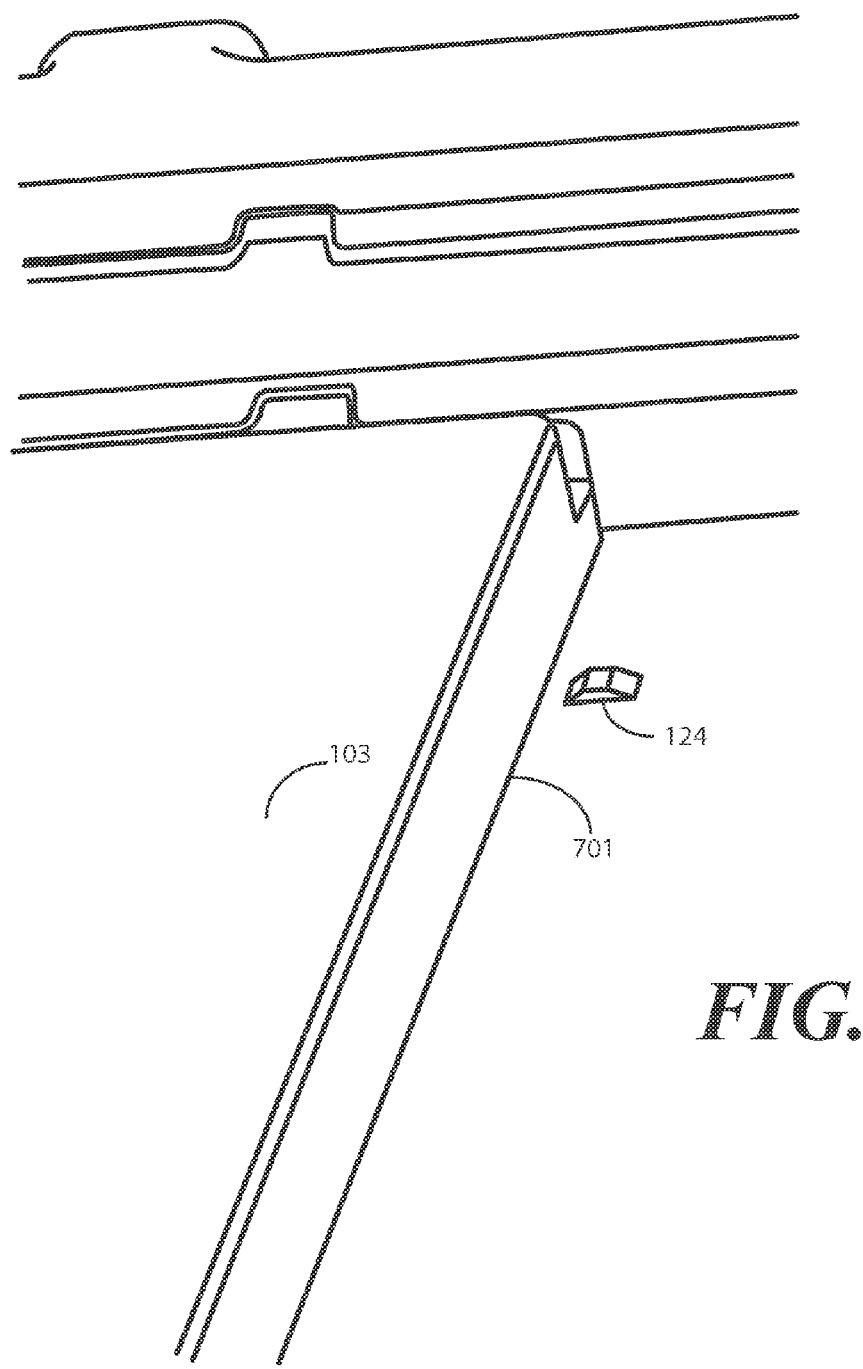
FIG. 7 illustrates a sliding door engaged in a track of a container engaging section of a lid, with the sliding door in a partially closed position in accordance with one or more embodiments of the disclosure.
Figure 8:
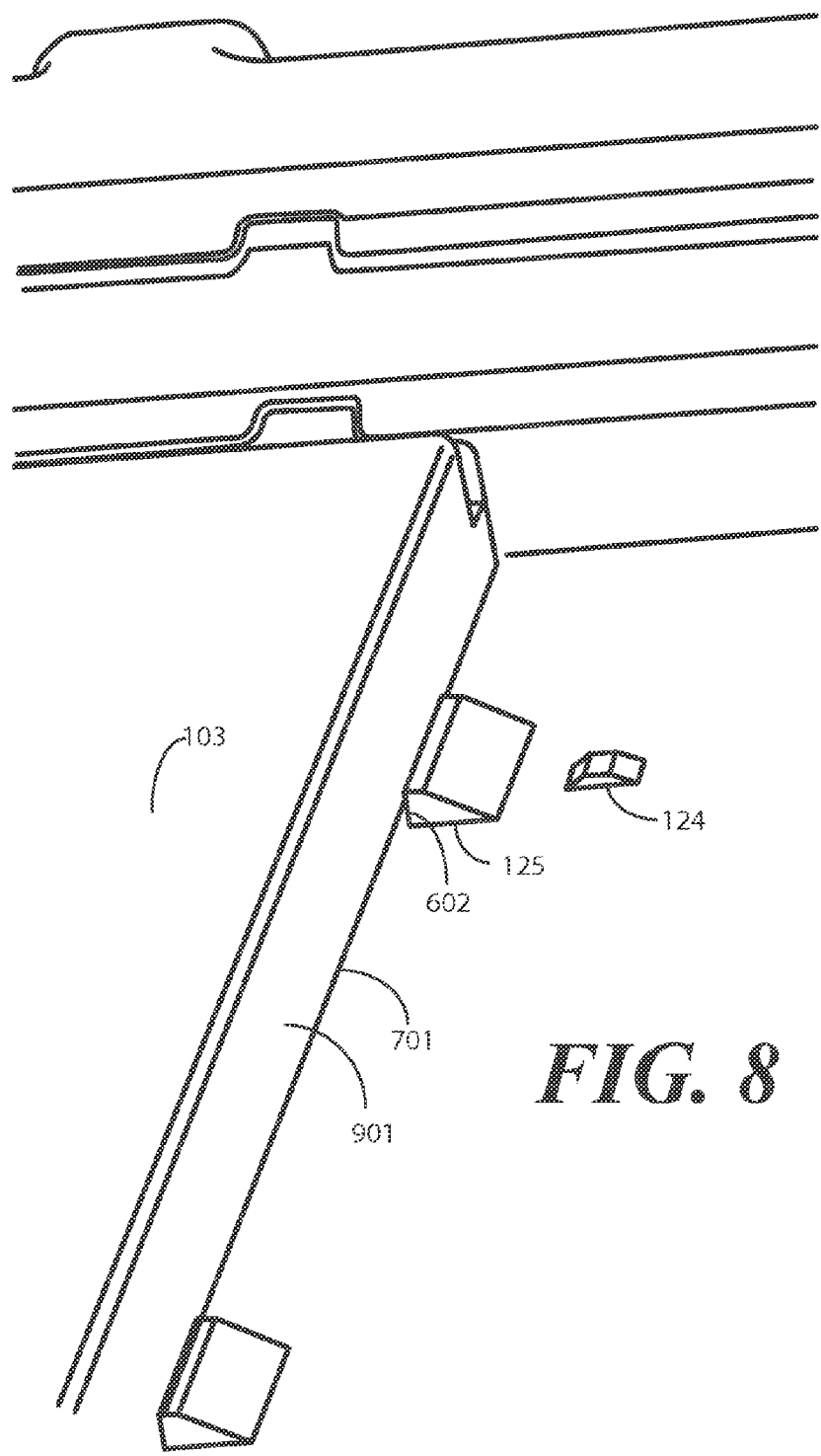
FIG. 8 illustrates a sliding door engaged in a track of a container engaging section of a lid, with the sliding door in a closed position in accordance with one or more embodiments of the disclosure.

Turning briefly to FIG. 7, the second sliding door 103 is shown in the partially closed position. In this position, the major protuberance (125) is disposed beneath the second sliding door 103. However, the minor protuberance 124 is not. Accordingly, an edge 701 of the second sliding door 103 is disposed between the minor protuberance 124 and the major protuberance (125). Turning to FIG. 8, the second sliding door 103 is shown in the closed position. In this position, the major protuberance 125 is disposed between the edge 701 of the second sliding door 103 and the minor protuberance 124. The trailing vertical surface 602 of the major protuberance 125 is biased against the rear sidewall 911 of the second sliding door 103 to retain the second sliding door 103 in the closed position.

Note that two major protuberances and only one minor protuberance are shown in FIG. 8, while a single major and minor protuberance were shown in FIG. 1. This is to demonstrate the flexibility with which embodiments of the disclosure can be constructed. One or more major protuberances can be included as necessary. Similarly, one or more minor protuberances can be included. The numbers of major and minor protuberances can be equal or different.

Turning now to FIGS. 11-14, the first sliding door 102 and the second sliding door 103 are shown in the open position 1100. In one embodiment, when the first sliding door 102 and the second sliding door 103 are in the open position 1100 the minor protuberance (124) and the major protuberance (125) are disposed beneath the second sliding door 103. In this illustrative embodiment, when the first sliding door 102 and the second sliding door 103 are in the open position 1100, the minor protuberance (124) and the major protuberance (125) are disposed beneath both the first sliding door 102 and the second sliding door 103. Movement of the second sliding door 103 in the opening direction 604 is limited by the sharps deposition well wall 111. Movement of the first sliding door 102 in the opening direction 604 is limited by engagement of the front side edge 401 of the first sliding door 102 with the interlocking protrusions (126).

Figure 11:
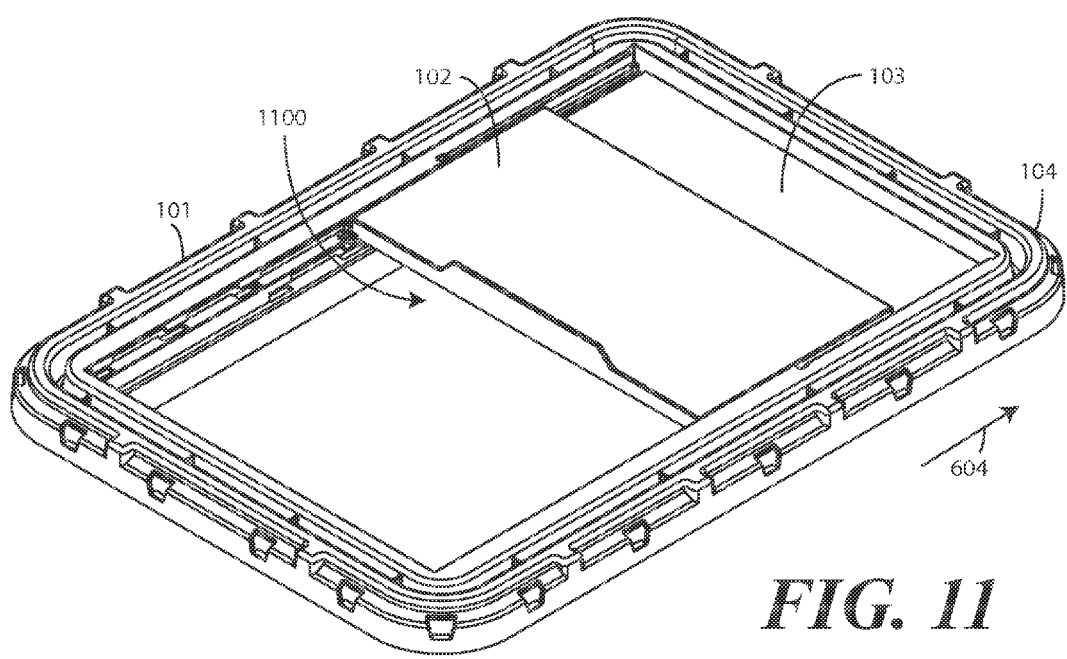
FIG. 11 illustrates a perspective view of a first sliding door and a second sliding door of one explanatory lid selectively moved to an open position in accordance with one or more embodiments of the disclosure.
Figure 12:
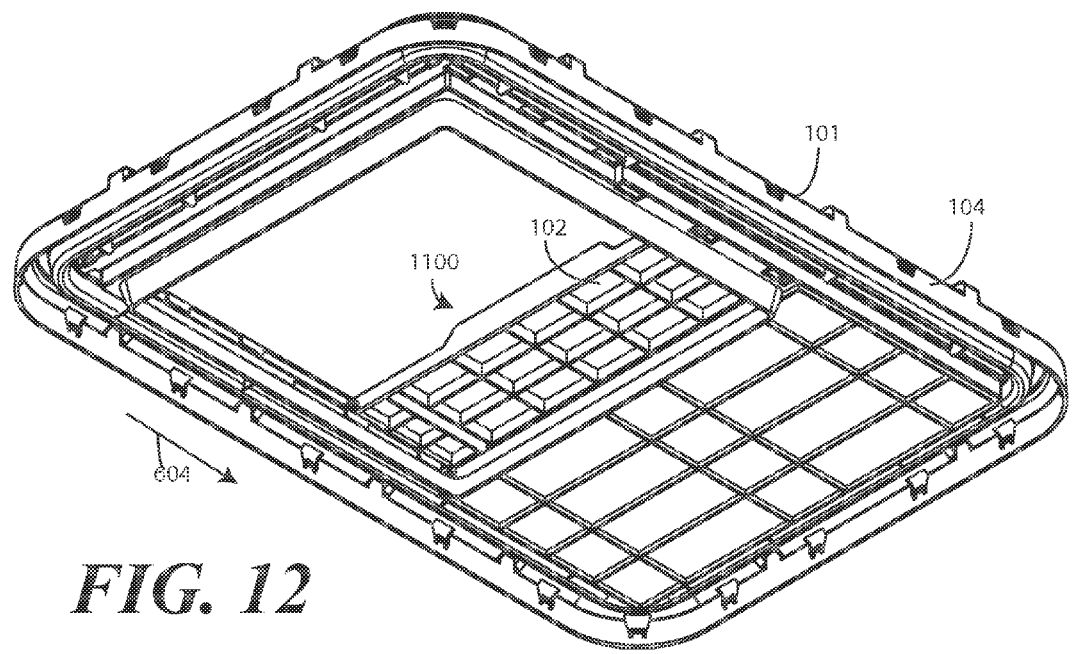
FIG. 12 illustrates another perspective view of a first sliding door and a second sliding door of one explanatory lid selectively moved to an open position in accordance with one or more embodiments of the disclosure.
Figure 13:
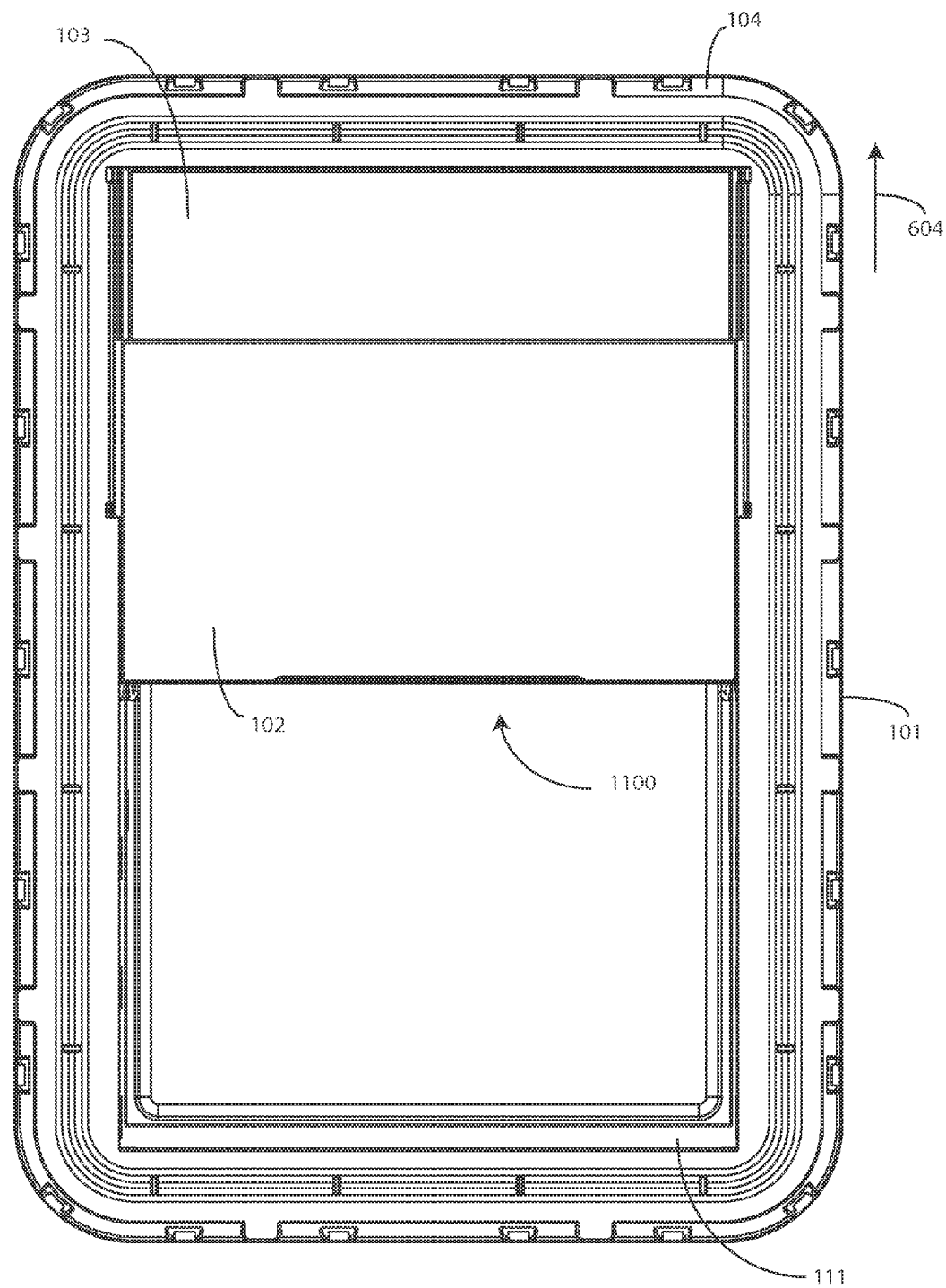
FIG. 13 illustrates a top plan view of a first sliding door and a second sliding door of one explanatory lid selectively moved to an open position in accordance with one or more embodiments of the disclosure.
Figure 14:
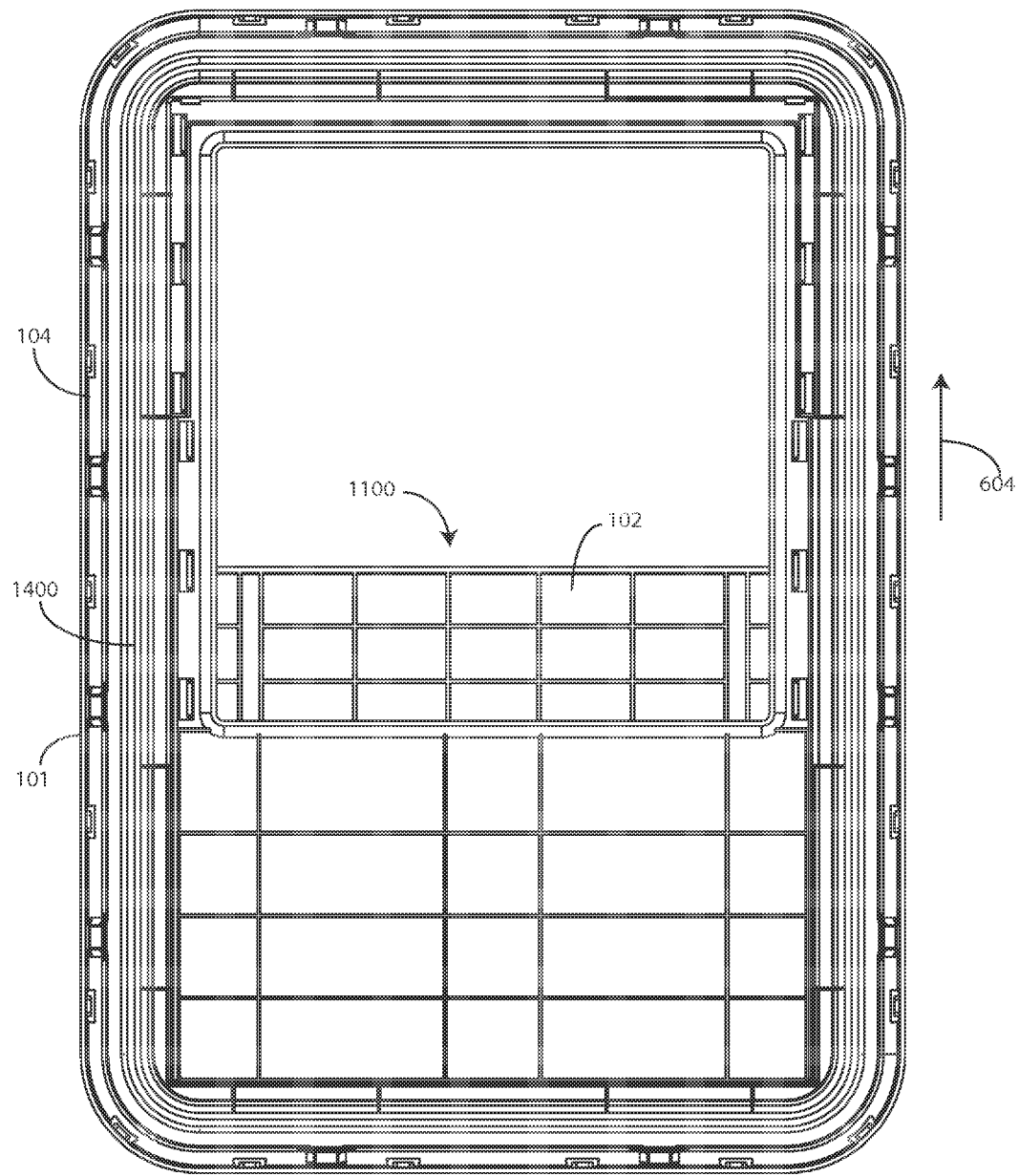
FIG. 14 illustrates a bottom plan view of a first sliding door and a second sliding door of one explanatory lid selectively moved to an open position in accordance with one or more embodiments of the disclosure.

FIGS. 12 and 14 illustrate a first side of the lid body 101, while FIGS. 11 and 13 illustrate a second side of the lid body 101 that is disposed opposite the first side. In this illustrative embodiment, the sliding surface (120) is disposed along the second side of the lid body 101. In one embodiment, as best shown in FIG. 14, the container engaging section 104 of the lid body 101 comprises a concave receiver 1400 disposed about the perimeter (106) along the first side of the lid body 101. The concave receiver 1400 receives the lip edge of a sharps container when the lid body 101 couples to the sharps container.

Figure 15:
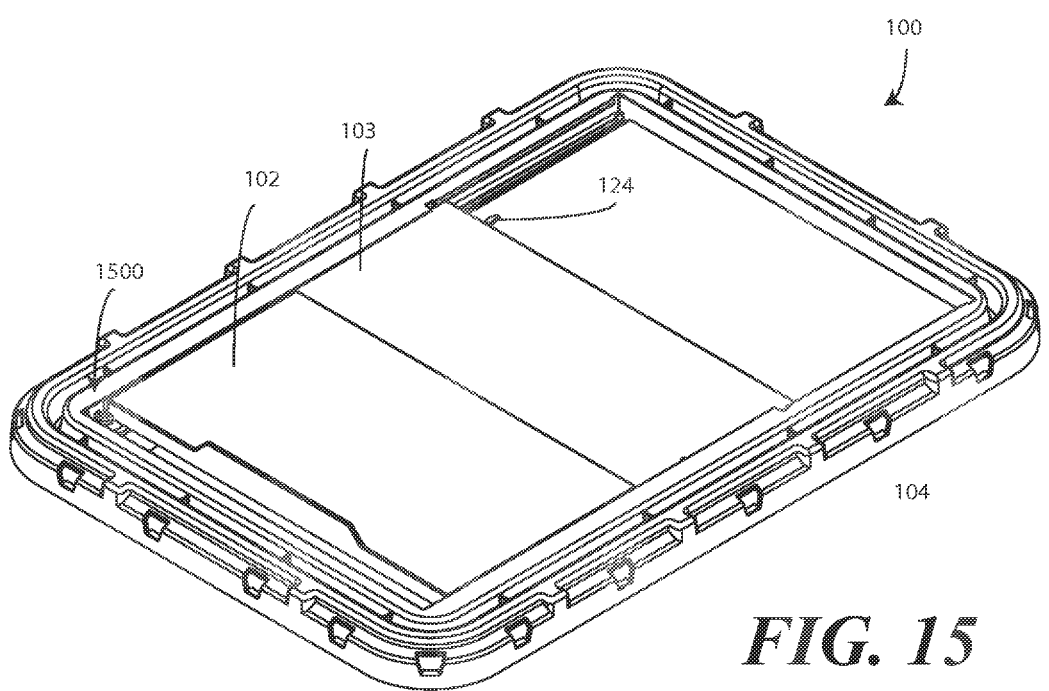
FIG. 15 illustrates a perspective view of a first sliding door and a second sliding door of one explanatory lid selectively moved to a partially closed position in accordance with one or more embodiments of the disclosure.
Figure 16:
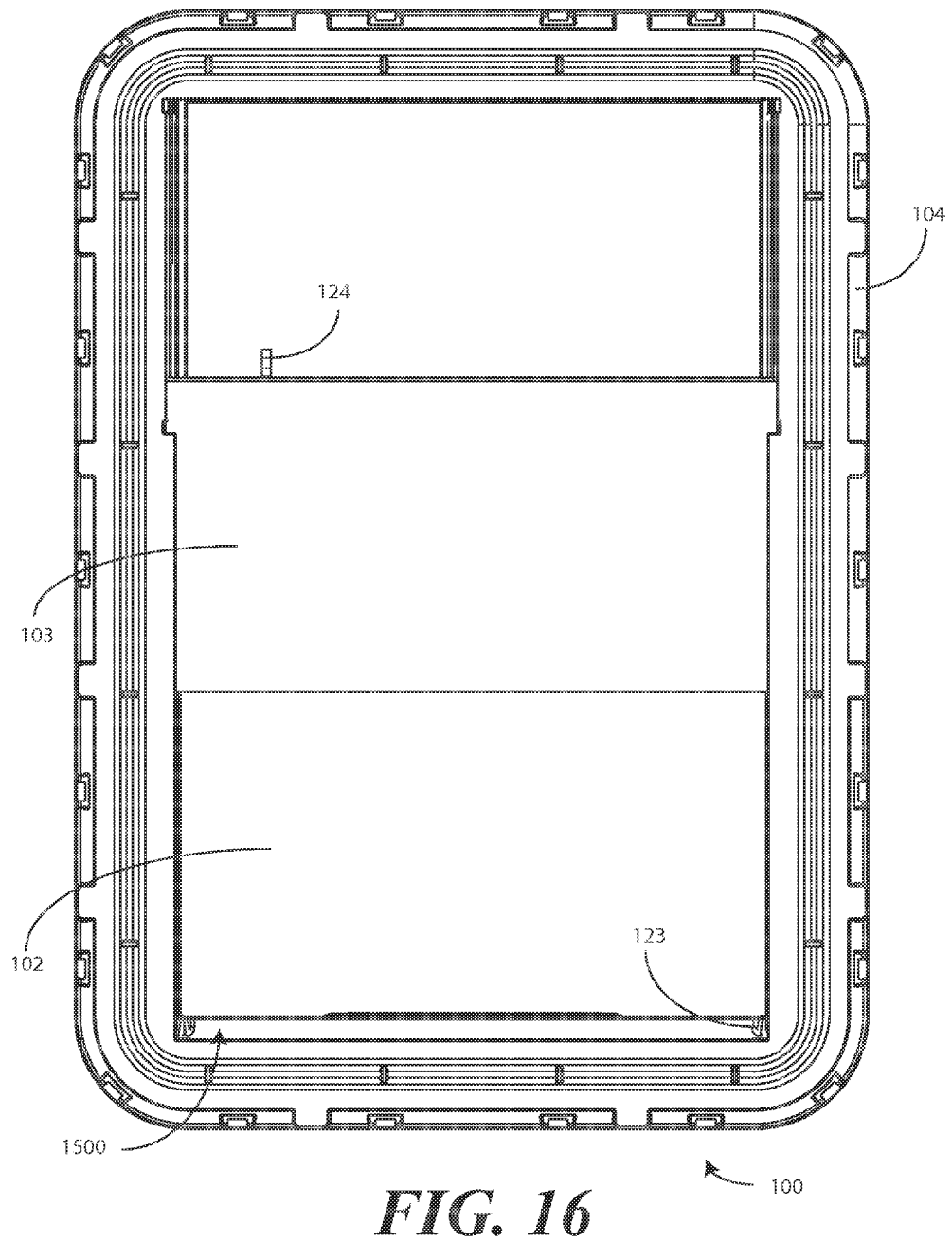
FIG. 16 illustrates a top plan view of a first sliding door and a second sliding door of one explanatory lid selectively moved to a partially closed position in accordance with one or more embodiments of the disclosure.

Turning now to FIGS. 15-16, the first sliding door 102 and the second sliding door 103 have been slid to the partially closed position 1500. In this position, the major protuberance (125) is disposed beneath the second sliding door 103. However, the minor protuberance 124 is not. Accordingly, an edge (701) of the second sliding door 103 is disposed between the minor protuberance 124 and the major protuberance (125). In this embodiment the partially closed position 1500 is configured such that the first sliding door 102 and the second sliding door 103 close to the maximum extent without the locking feature 123 engaging the interior sidewall 502 of the container engaging section 104. This prevents a user from inadvertently being harmed by touching sharps disposed beneath the lid 100. This prevents the user from being exposed to disease or other microbe that may have been carried by a patient upon whom the sharps were used. By providing the partially closed position 1500 users, personnel, and others are advantageously prevented from being accidently punctured, or cut, and thus exposed to infection by the disease pathogens.

Figure 17:
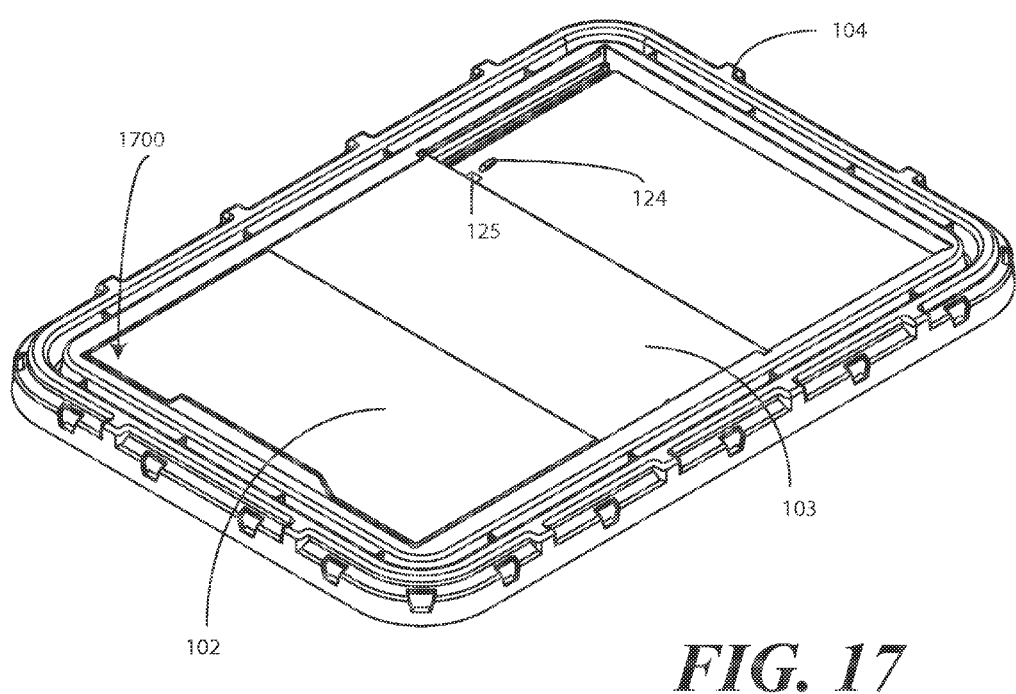
FIG. 17 illustrates a perspective view of a first sliding door and a second sliding door of one explanatory lid selectively moved to a closed position in accordance with one or more embodiments of the disclosure.
Figure 18:
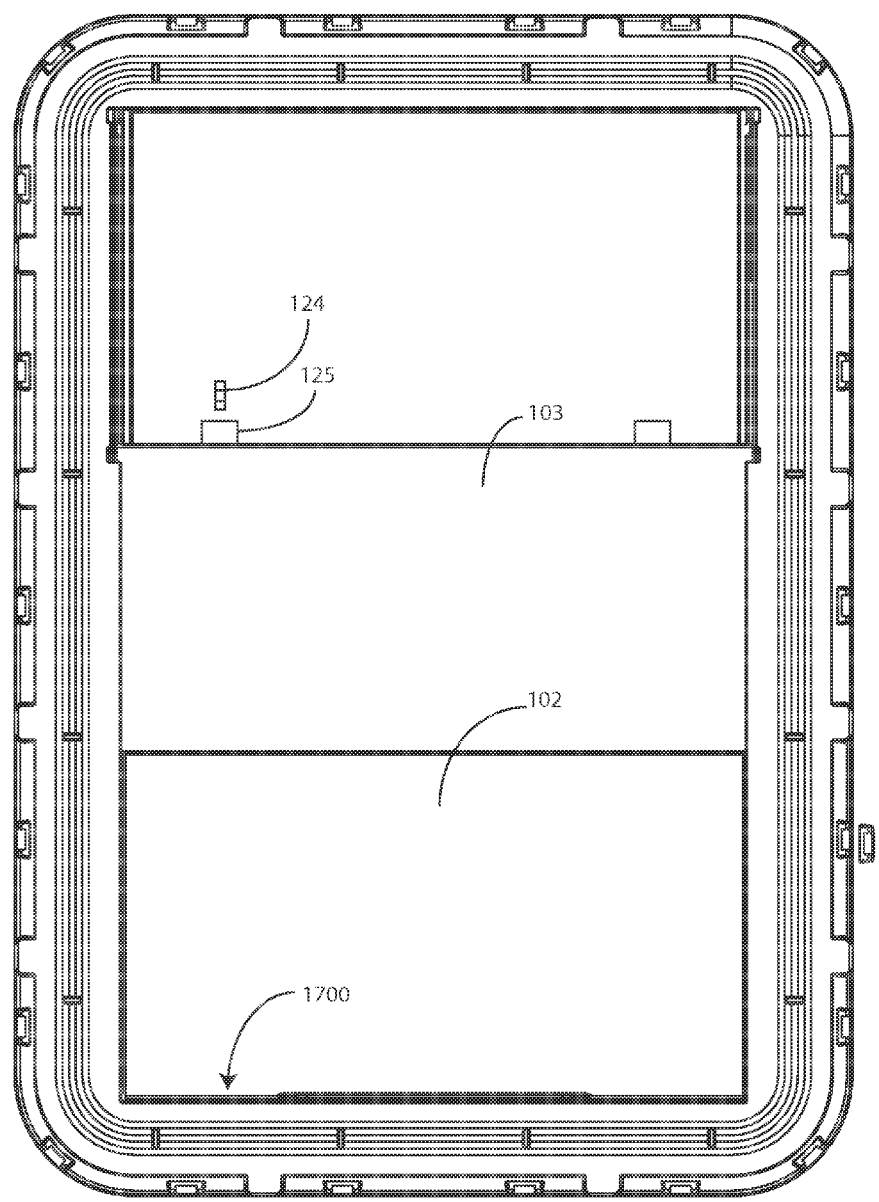
FIG. 18 illustrates a top plan view of a first sliding door and a second sliding door of one explanatory lid selectively moved to a closed position in accordance with one or more embodiments of the disclosure.

Turning now to FIGS. 17-18, the first sliding door 102 and the second sliding door 103 have been slid to the closed position 1700. In this position, the major protuberance 125 is disposed between the edge (701) of the second sliding door 103 and the minor protuberance 124. The trailing vertical surface (602) of the major protuberance 125 is biased against the rear sidewall 911 of the second sliding door 103 to retain the second sliding door 103 in the closed position 1700. Additionally, the locking feature (123) is engaged with the interior sidewall (502) of the container engaging section 104, thereby perdurably locking the first sliding door 102 to the container engaging section 104 when the first sliding door 102 and the second sliding door 103 are in the closed position 1700. This results in the first sliding door 102 and the second sliding door 103 sealing the sharps disposal aperture (119) when in the closed position 1700.

Figure 19:
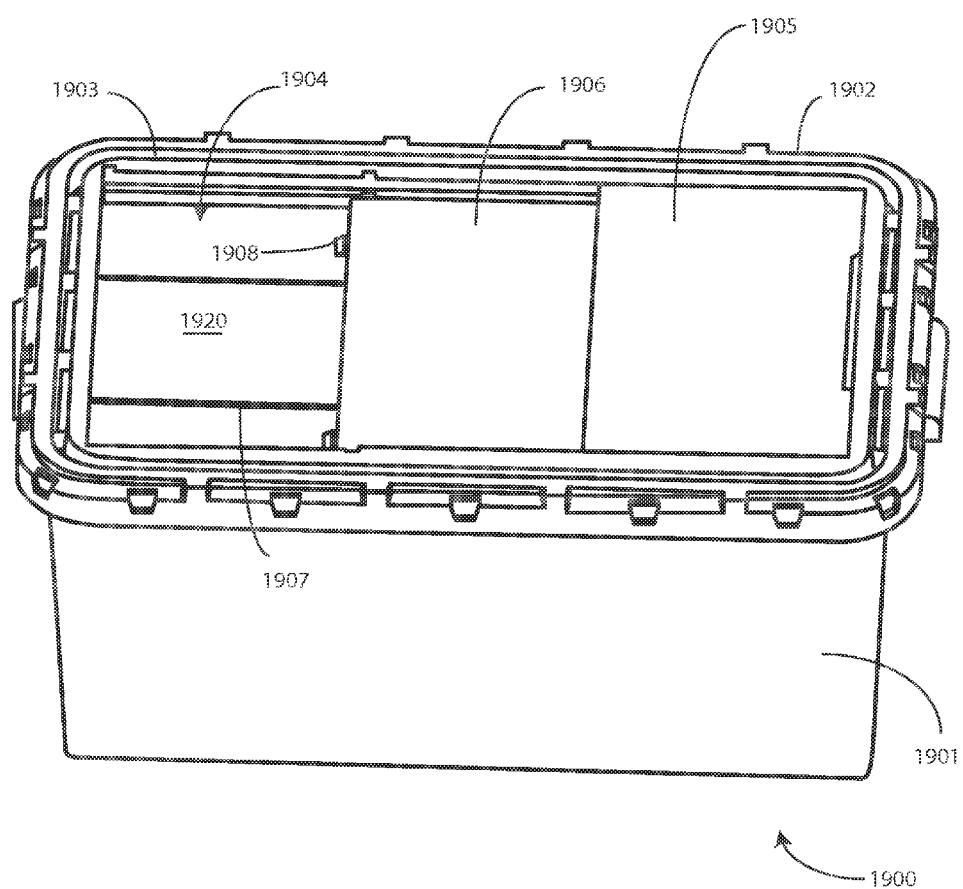
FIG. 19 illustrates one explanatory sharps container and lid in accordance with one or more embodiments of the disclosure.

Turning now to FIG. 19, illustrated therein is one explanatory sharps disposal container 1900 configured in accordance with one or more embodiments of the disclosure. The sharps disposal container 1900 comprises a container 1901 to hold sharps for disposal and a lid 1902.

The lid 1902 comprises a container engaging section 1903 to couple the lid 1902 to the container 1901. The lid 100 also comprises an interior section 1904 disposed within a perimeter of the lid 1902 defined by the container engaging section 1903. The interior section 1904 defines a planar surface 1920 spanning a minority of the interior section 1904 and an aperture to receive the sharps for disposal. In this embodiment, the aperture is disposed beneath a first sliding door 1906 and a second sliding door 1905. The aperture of this embodiment spanning a majority, but less than seventy percent, of the interior section 1904. In this embodiment, the planar surface 1920 comprises a minor protuberance disposed in a groove 1907 and a major protuberance 1908. The minor protuberance is disposed in the groove 1907 as described above with reference to FIG. 9.

As shown, the first sliding door 1906 is interlocked between the second sliding door 1905 and the planar surface 1920. As described above with reference to other embodiments, the first sliding door 1906 and the second sliding door 1905 are each selectively moveable between one of three positions.

A first position is the open position. In this position the minor protuberance and the major protuberance 1908 are disposed beneath at least the first sliding door 1906. A second position is a partially closed position. In this position, an edge of the first sliding door 1906 is disposed between the minor protuberance and the major protuberance 1908. A third position is a closed position. In this position, the major protuberance 1908 is disposed between the edge of the first sliding door 1906 and the minor protuberance.

In the foregoing specification, specific embodiments of the present disclosure have been described. However, one of ordinary skill in the art appreciates that various modifications and changes can be made without departing from the scope of the present disclosure as set forth in the claims below. Thus, while preferred embodiments of the disclosure have been illustrated and described, it is clear that the disclosure is not so limited. Numerous modifications, changes, variations, substitutions, and equivalents will occur to those skilled in the art without departing from the spirit and scope of the present disclosure as defined by the following claims. Accordingly, the specification and figures are to be regarded in an illustrative rather than a restrictive sense, and all such modifications are intended to be included within the scope of present disclosure. The benefits, advantages, solutions to problems, and any element(s) that may cause any benefit, advantage, or solution to occur or become more pronounced are not to be construed as a critical, required, or essential features or elements of any or all the claims.

What is claimed is:

1. A lid for a sharps container, the lid comprising:
a first sliding door and a second sliding door; and
a lid body, comprising:
a container engaging section defining:
a perimeter of the lid;
a first track to receive the first sliding door; and
a second track to receive the second sliding door;
wherein the first track is longer than the second track; and
an interior section extending from the container engaging section within the perimeter, the interior section defining:
a sharps disposal aperture spanning a majority of the interior section;
a sliding surface spanning a minority of the interior section;
a minor protuberance disposed along the interior section; and
a major protuberance disposed along the interior section proximally with the minor protuberance;
the second sliding door to interlock between the sliding surface and the first sliding door, the first sliding door and the second sliding door selectively slidable between:
an open position with the minor protuberance and the major protuberance disposed beneath the second sliding door;
a partially closed position with an edge of the second sliding door disposed between the minor protuberance and the major protuberance; and
a closed position with the major protuberance disposed between the edge of the second sliding door and the minor protuberance.

2. The lid of claim 1, each of the first sliding door and the second sliding door defining a major face having less area than the sharps disposal aperture.

3. The lid of claim 1, the sliding surface substantially planar.

4. The lid of claim 1, where when the first sliding door and the second sliding door are in the open position, the minor protuberance and the major protuberance are disposed beneath both the first the second sliding door.

5. The lid of claim 1, the major protuberance defining a single-sided ramp.

6. The lid of claim 5, the minor protuberance defining a double-sided ramp.

7. The lid of claim 6, the first sliding door comprising one or more cantilevered hooks to perdurably lock the first sliding door to the container engaging section when the first sliding door and the second sliding door are in the closed position.

8. The lid of claim 5, the first sliding door and the second sliding door to seal the sharps disposal aperture when in the closed position.

9. The lid of claim 1 and the second track each comprising engaging sections engaging the first sliding door and the second sliding door, respectively.

10. The lid of claim 9, each of the first track and the second track defining one or more flanges to retain the first sliding door and the second sliding door within the first track and the second track, respectively.

11. The lid of claim 10, each of the first sliding door and the second sliding door defining a groove to receive the one or more flanges.

12. The lid of claim 1, the first sliding door further comprising flange, the first sliding door to slide in response to force applied to the flange.

13. The lid of claim 12, the second sliding door comprising one or more interlocking protrusions to retain the second sliding door interlocked between the sliding surface and the first sliding door when the first sliding door slides relative to the second sliding door.

14. The lid of claim 1, the perimeter substantially rectangular.

15. The lid of claim 1, the container engaging section defining a concave receiver disposed about the perimeter along a first side of the lid body, the sliding surface disposed along a second side of the lid body.

16. The lid of claim 1, the minor protuberance disposed within a groove.

17. The lid of claim 16, the second sliding door defining a flange to insert into the groove to engage the minor protuberance when the second sliding door transitions from the open position to the partially closed position.

18. The lid of claim 1, the minority of the interior section less than or equal to one third of an area defined by the interior section.

19. The sharps disposal container of claim 18, the second sliding door comprising one or more cantilevered hooks to perdurably lock the second lid to the container engaging section when the first sliding door and the second sliding door are in the closed position.

20. A lid for a sharps container, the lid comprising:
a first sliding door and a second sliding door; and
a lid body, comprising:
  a container engaging section defining:
    a perimeter of the lid;
    a first track to receive the first sliding door; and
    a second track to receive the second sliding door; and
  an interior section extending from the container engaging section within the perimeter, the interior section defining:
    a sharps disposal aperture spanning a majority of the interior section;
    a sliding surface spanning a minority of the interior section;
    a minor protuberance disposed along the interior section, the minor protuberance defining a double-sided ramp; and
    a major protuberance disposed along the interior section proximally with the minor protuberance, the major protuberance defining a single-sided ramp;
the second sliding door to interlock between the sliding surface and the first sliding door, the first sliding door and the second sliding door selectively slidable between:
  an open position with the minor protuberance and the major protuberance disposed beneath the second sliding door;
  a partially closed position with an edge of the second sliding door disposed between the minor protuberance and the major protuberance; and
  a closed position with the major protuberance disposed between the edge of the second sliding door and the minor protuberance.

\* \* \* \* \*